(12) United States Patent
Gonda et al.

(10) Patent No.: US 7,244,714 B1
(45) Date of Patent: *Jul. 17, 2007

(54) METHODS OF DELIVERING AEROSOLIZED POLYNUCLEOTIDES TO THE RESPIRATORY TRACT

(75) Inventors: Igor Gonda, San Francisco, CA (US); Hans Schreier, Sebastopol, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/330,903

(22) Filed: Jun. 11, 1999

Related U.S. Application Data

(60) Provisional application No. 60/089,146, filed on Jun. 12, 1998.

(51) Int. Cl.
*A61K 31/70* (2006.01)
*A61K 9/127* (2006.01)
(52) U.S. Cl. .................... 514/44; 424/450; 530/350
(58) Field of Classification Search .......... 128/200.14, 128/203.21, 202.23, 207.14; 702/104; 424/450; 514/44
See application file for complete search history.

(56) References Cited

U.S. PATENT DOCUMENTS

| | | | | |
|---|---|---|---|---|
| 5,049,389 A | * | 9/1991 | Radhakrishnan | 424/450 |
| 5,333,106 A | * | 7/1994 | Lanpher | 600/538 |
| 5,404,871 A | | 4/1995 | Goodman et al. | 128/200.14 |
| 5,450,336 A | | 9/1995 | Rubsamen et al. | 702/104 |
| 5,458,136 A | * | 10/1995 | Jaser et al. | 128/200.14 |
| 5,474,059 A | * | 12/1995 | Cooper | 128/200.22 |
| 5,497,763 A | * | 3/1996 | Lloyd | 128/200.14 |
| 5,522,385 A | * | 6/1996 | Lloyd | 128/203.26 |
| 5,547,932 A | * | 8/1996 | Curiel et al. | 435/65 |
| 5,589,466 A | | 12/1996 | Felgner et al. | 514/44 |
| 5,718,222 A | | 2/1998 | Lloyd et al. | 128/200.14 |
| 5,724,957 A | | 3/1998 | Rubsamen et al. | |
| 5,736,327 A | * | 4/1998 | Collins | 435/6 |
| 5,756,353 A | * | 5/1998 | Debs | 514/44 |
| 5,795,587 A | * | 8/1998 | Gao et al. | 424/450 |
| 5,803,078 A | | 9/1998 | Brauner | 128/207.14 |
| 5,819,726 A | | 10/1998 | Rubsamen et al. | 128/200.14 |
| 5,823,178 A | | 10/1998 | Lloyd et al. | 128/200.14 |
| 5,829,435 A | | 11/1998 | Rubsamen et al. | 128/203.21 |
| 5,849,719 A | | 12/1998 | Carson et al. | 514/44 |
| 5,906,202 A | | 5/1999 | Schuster et al. | 128/203.23 |
| 5,908,777 A | * | 6/1999 | Lee et al. | 435/320.1 |
| 5,948,681 A | * | 9/1999 | Scanlin et al. | 435/455 |
| 5,976,567 A | * | 11/1999 | Wheeler et al. | 424/450 |
| 5,994,314 A | * | 11/1999 | Eljamal | 514/44 |
| 5,994,315 A | * | 11/1999 | Nyce et al. | 514/44 |
| 6,008,202 A | * | 12/1999 | Huang et al. | 514/44 |
| 6,030,834 A | * | 2/2000 | Chu et al. | 435/325 |
| 2003/0124093 A1 | * | 7/2003 | Rothenpieler et al. | 424/85.2 |

FOREIGN PATENT DOCUMENTS

| | | |
|---|---|---|
| WO | WO 94/27653 | 12/1994 |
| WO | WO 96/13161 | 5/1996 |
| WO | WO 96/40963 | 12/1996 |
| WO | WO 96/41873 | 12/1996 |

OTHER PUBLICATIONS

Yonemitsu et. al.; HVJ (Sendai virus)-cationic liposomes: a novel and potentially effective liposome-mediated technique for gene transfer to the airway epithelium, 1997, Gene Therapy 4: 631-638.*
Gagne et. al.; Aerosolization of Plasmid DNA Protective Effects of Solute, Condensing Agents, and Liposome Carriers, 1997, Proceed Int'l Symp. Control Rel. Bioact. Mater, 641-642.*
Mitchell et. al.; Induction of mucosal anti-HIV antibodies by facilitated transfection of airway epithelium with lipospermine/DNA complexes; 1995, Immunotechnology 1: 211-219.*
Crook et. al.; Plasmid DNA molecules complexed with cationic liposomes are protected from degradation by nucleases and shearing by aerosolisation, 1996, Gene Therapy3: 834-839.*
McLachlan et. al.; Evaluation in vitro and in vivo of vationic liposome-expression construct complex es for cystic fibrosis gene therapy, 1995, Gene Therapy2: 614-622.*
Saravolac et al (J. Drug Targ. 7(6): 423-437, 2000).*
Tang et al (Gene Therapy, 4: 823-832, 1997), abstract and Fig. 4 on p. 832).*
Mack (Am. J. Med. Sci. 307(2): 138-143, 1992).*
Patil et al (AAPS Journal 6(4): 1-10, 2004).*
Brigham et al. (1994), "Gene Therapy for Inflammatory Diseases," *Prog. Clin. Biol. Res.*, vol. 388:361-365.
Cannizzo et al. (Jun. 1997), "Augmentation of Blood Platelet Levels by Intratracheal Adminstration of an Adenovirus Vector Encoding Human Thrombopoietin cDNA," *Nature Biotechnology*, vol. 15:570-573.
Canonico et al. (1994), "Aerosol and Intravenous Transfection of Human α1-Antitrypsin Gene to Lungs of Rabbots," *Am. J. Respir. Cell. Mol. Biol.*, vol. 10:24-29.

(Continued)

*Primary Examiner*—Richard Schnizer
(74) *Attorney, Agent, or Firm*—Karl Bozicevic; Bozicevic, Field & Francis LLP

(57) ABSTRACT

Methods and devices for delivering aerosolized formulations containing polynucleotides to specified regions within a subject's respiratory tract are disclosed. The methods find use in the delivery of ribozymes, antisense polynucleotides, and DNA and RNA expression vectors into airway epithelial cells, alveoli, pulmonary macrophages and other cells in the respiratory tract (including the oropharynx, nose, nasopharynx). These methods may be used for optimization of transfection efficiency and expression in vivo, and for in vivo expression, for example for generating an immune response, or inducing immunological tolerance.

6 Claims, 3 Drawing Sheets

OTHER PUBLICATIONS

Erzurum et al. (1993), "Protection of Human Endothelial Cells from Oxidant Injury by Adenovirus-Mediated Transfer of the Human Catalase cDNA," *Nucl. Acid. Res.*, vol. 21(7):1607-1612.

Fujiwara et al. (Oct. 1994), "Therapeutic Effect of a Retroviral Wild-Type p53 Expression Vector in an Orthotopic Lung Cancer Model," *J. Natl. Cancer Inst.*, vol. 86(19):1458-1462.

Knoell et al. (1995), "Clinical Implications of Gene Therapy for $Alpha_1$-Antitrypsin Deficiency," *Chest*, vol. 107:535-545.

Kolls et al. (Mar. 1995), "Adenovirus-Mediated Blockade of Tumor Necrosis Factor in Mice Protects Against Endotoxic Shock Yet Impairs Pulmonary Host Defects," *J. Infect. Dis.*, vol. 171:570-575.

McDonald et al. (Mar. 1997), "Safety of Airway Gene Transfer with Ad2/CFTR2: Aerosol Administration in the Nonhuman Primate," *Human Gene Therapy*, vol. 8:411-422.

Patapoff and Gonda (1997) "Inhalation Delivery of Therapeutic Peptides and Proteins," A. Adjei and P. Gupta, eds., Marcel Dekker, Inc., pp. 493-514.

Porteous et al. (1997,) "Evidence for Safety and Efficacy of DOTAP Cationic Liposome Mediated CFTR Gene Transfer to the Nasal Epithelium of Patients with Cystic Fibrosis," *Gene Therapy*, vol. 4: 210-218.

Rosenfeld et al. (Apr. 1991), "Adenovirus-Mediated Transfer of a Recombinant α1-Antitrypsin Gene to the Lung Epithelium in Vivo," *Science*, vol. 252:431-434.

Schuster et al. (1997), "The $AER_x$ Aerosol Delivery System," *Pharm. Res.*, vol. 14(3):354-357.

Smith et al. (1994), "Surfactant Protein A-Directed Toxin Gene Kills Ling Cancer Cells In Vitro," *Hum. Gene Ther.*, vol. 5:29-35.

* cited by examiner

US 7,244,714 B1

METHODS OF DELIVERING AEROSOLIZED POLYNUCLEOTIDES TO THE RESPIRATORY TRACT

CROSS-REFERENCE TO RELATED APPLICATIONS

This application is the non-provisional conversion of provisional U.S. Patent Application Ser. No. 60/089,146, filed Jun. 12, 1998, the contents of which is incorporated by reference in its entirety.

GOVERNMENT RIGHTS

The United States Government may have certain rights in the present application to pursuant NIH Grant 1 R43 HL57770-01.

FIELD OF THE INVENTION

This invention relates generally to methods for delivering aerosolized formulations containing polynucleotides. More specifically, this invention relates to methods for delivering aerosolized formulations containing a naked or formulated and condensed polynucleotide to a specific area of the respiratory tract.

BACKGROUND OF THE INVENTION

Pulmonary drug delivery is an attractive alternative to oral, transdermal, and parenteral administration because self-administration is simple, there is no first-pass liver effect of absorbed drugs, and there is reduced enzymatic activity and pH-mediated drug degradation associated with the oral route. Furthermore, structural and physiological features of the lung, including a large mucosal surface and intricate branching for drug absorption, make aerosolization a desirable method for delivering therapeutic agents to the lung.

The mammalian respiratory tract can be divided into the upper airways, including the oropharynx, larynx and trachea; the central airways, including the bronchi and bronchioli; and the deep lung, including the alveoli. The lung is the site of many severe, chronic, life-threatening diseases such as chronic bronchitis, asthma, emphysema, lung cancer, and persistent pulmonary infections of various origins.

Several conventional pharmaceutical therapies for pulmonary diseases could be supplanted by gene transfer therapies. For example, studies have been conducted to assess the feasibility of gene therapeutic approaches to treating cystic fibrosis (CF) to correct deficiencies in the CFTR protein (McDonald et al. (1997) *Hum. Gene Ther.* 8:411–422; and Porteous et al. (1997) *Gene Therapy* 4:210–218); emphysema associated with α1-antitrypsin deficiency (Rosenfeld et al. (1991) *Science* 252:431–434; Canonico et al. (1994) *Am. J. Respir. Cell. Mol. Biol.* 10:24–29; and Knoell and Wewers (1995) *Chest* 107:535–545); oxygen injury (Erzurum et al. 91993) *Nucl. Acids Res.* 21:1607–1612); lung cancer (Smith et al. (1994) *Hum. Gene Ther.* 5:29–35; and Fujiwara et al. (1994) *J. Natl. Cancer Inst.* 86(19):1458–1462); and general inflammatory pulmonary conditions (Kolls et al. (1995) *J. Infect. Dis.* 171:570–575; and Brigham et al. (1994) *Prog. Clin. Biol. Res.* 388: 361–365).

In vivo systemic expression of genetic material introduced into the respiratory tract has also been used to provide therapeutically effective levels of a secreted cytokine. Cannizzo et al. ((1997) *Nature Biotechnol.* 15:570–573) administered an adenovirus vector, containing a human thrombopoietin cDNA under control of a CMV promoter, into the trachea of BALB/c mice. Within a week after treatment, human thrombopoietin was seen in the serum, platelet levels increased over six-fold, and megakaryocytosis was seen in the bone marrow.

Another therapeutic approach involving polynucleotide administration is the generation of an immune response in the absence of a viral vaccine. Introduction of expression vectors into animals generates an immune response to the expressed protein. U.S. Pat. No. 5,589,466. This technique is useful, for example, where a viral vaccine is difficult to produce, or a nonpathogenic strain of the virus is not available. Administration of such expression vectors to the lung can yield immune responses without the disadvantages associated with injections, and may be directed to pathogens affecting the respiratory tract such as influenza virus, respiratory syncytial virus, hantavirus or adenovirus, and respiratory tract disorders such as asthma. Expression vectors can also be used to induce immune tolerance. U.S. Pat. No. 5,849,719.

Delivery of various therapeutic agents, particularly macromolecules, to the respiratory tract has proved challenging. Some of the difficulties encountered include excessive loss of inhaled drug in the oropharyngeal cavity, phagocytosis by lung macrophages, and poor control over the site of deposition. Selective delivery into various parts of the respiratory tract by "focal" methods such as microspray into limited anatomical regions (e.g., nasal or oral cavity, selected airways) has been attempted. Patapoff and Gonda (1997) in "Inhalation Delivery of Therapeutic Peptides and Proteins", A. Adjei and P. Gupta, eds., Marcel Dekker, Inc. Other methods include endotracheal catheterization (U.S. Pat. No. 5,803,078). To date, however, no method has been shown to be adequate for the reproducible delivery of polynucleotides to specified portions of the respiratory tract. In addition, delivery to the lung of polynucleotide therapeutics has proved more difficult than delivery of small molecule therapeutics, in part due to the larger size of polynucleotides and their greater susceptibility to physical disruption from the forces required to generate an aerosol, thereby hindering or preventing efficient therapy.

There is currently a need for improved methods for delivery of polynucleotides to particular regions of the mammalian respiratory tract. The current invention addresses these needs and provides related advantages as well.

SUMMARY OF THE INVENTION

Figure 1:
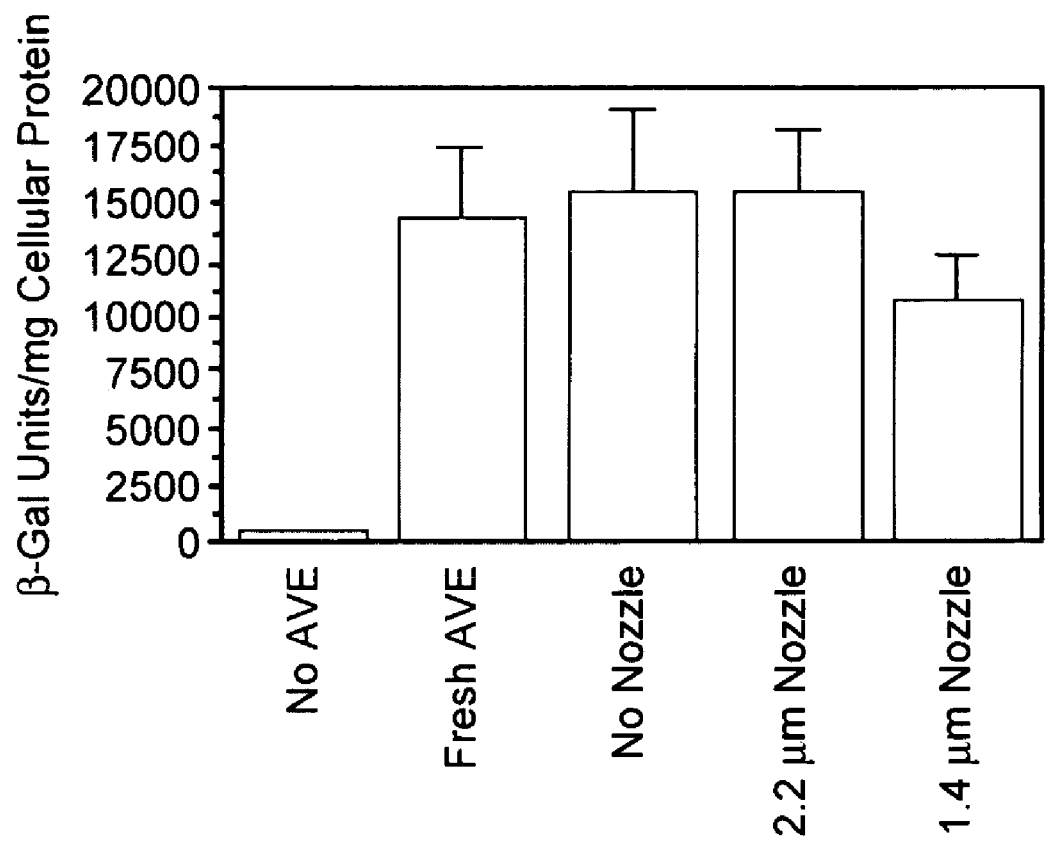
FIG. 1 is a graph depicting transfection rates, expressed as β-Gal units per mg cellular protein, of AVE/DNA formulations extruded through pores of various sizes, then transfected into 293 cells in vitro.

The present invention provides methods for delivering aerosolized polynucleotides preferentially to a specified region of the mammalian respiratory tract. The methods are useful for delivering polynucleotides including those having therapeutic value to treat disorders specific to particular areas of the respiratory tract, and can further be used to deliver polynucleotides systemically, via the respiratory tract. The different areas of the respiratory tract can be targeted by (1) adjusting the size of particles of aerosol and/or (2) adjusting the volume inhaled during delivery. Particle size may be adjusted by changing the size of the pores of a membrane through which a liquid formulation is forced and/or by adding heat to evaporate carrier away and decrease particle size. Alternatively, particle size can be adjusted by using dry powder particles of the desired size. Inhaled volume can be adjusted merely by coaching a patient to inhale a given amount or by electronically measuring inhaled volume and providing a shut off means and/or signal means when a desired volume was reached.

In some embodiments, the polynucleotides delivered by the methods of the present invention are delivered in non-viral delivery vehicles. The polynucleotide delivered to the respiratory tract may be a therapeutic polynucleotide. In some of these embodiments, aerosols contain naked or formulated and condensed polynucleotides. In other embodiments, polynucleotides are associated with artificial viral envelopes. Polynucleotides delivered by the present methods can be used to deliver ribozymes, antisense molecules or antisense expression constructs which prevent expression of an undesirable cell product, such as elastase in the case of homozygous α1-antitrypsin deficiency. They can be used to deliver expression constructs encoding cellular proteins. In one embodiment, the polynucleotide encodes a CFTR, for delivery to a subject with cystic fibrosis. They can be used to express secreted proteins. In one embodiment, the polynucleotide encodes an α1-antitrypsin, for delivery to a subject who is deficient in α1-antitrypsin production. Other examples of secreted proteins that may be generated in lungs and secreted into the systemic circulation include cytokines, growth factors, and hormones such as calcitonin and insulin. Aerosolized polynucleotides can also be used to generate immune responses to expressed proteins, or to induce immune tolerance to an antigen. Delivery of aerosols to the nose may be used in the treatment of allergic rhinitis.

Aerosols may be used to transport naked or condensed and formulated polynucleotides via the lung into lymph, blood and macrophages or other cells of the body. Additionally, purified particles containing naked or formulated and condensed polynucleotides may be generated and isolated following aerosolization for diagnostic and therapeutic approaches, and for research into the structure of condensed polynucleotides. Aerosolization may also be used to generate low passage transformed cell lines, by introducing the polynucleotide in vivo, followed by isolation of cells from the subject.

In the methods of the present invention, preferential delivery is generally achieved by controlling the size of the aerosolized particle containing a polynucleotide. In some embodiments, methods are provided for delivering an aerosolized polynucleotide preferentially to the deep lung, i.e., the alveoli. In these embodiments, a majority of the aerosolized, polynucleotide-containing particles have a size in the range of 1–3 μm. In some embodiments, methods are provided for delivering an aerosolized polynucleotide preferentially to the central airways, i.e., the bronchi and bronchioles. In these embodiments, a majority of the aerosolized, polynucleotide-containing particles have a size in the range of 4–6 μm. In still other embodiments, methods are provided for delivering an aerosolized polynucleotide preferentially to the upper respiratory tract, including the oropharyngeal region and the trachea. In these embodiments, a majority of the aerosolized, polynucleotide-containing particles have a size in the range of 7–10 μm.

When treating many respiratory diseases, it may be desirable to deliver the aerosolized agent only to large airways of the lung referred to as the "central airways". More specifically, it may not be desirable to deliver aerosolized polynucleotides to the outer peripheral areas of the lung (into the alveoli), the mouth, or the trachea. However, the aerosol should be delivered to the alveoli if delivery to the circulatory system is desired and to obtain such the particle size should be about 1 to about 3 microns, provided the particle has a density similar to water, and a generally spherical shape. Particles with higher or lower density will effectively behave as bigger or smaller particles, respectively. Similarly, diseases of small airways and alveoli (e.g., asthma, emphysema, pulmonary infections, etc.) may also require delivery with small particles.

Particle size can be controlled by various means. In some embodiments, particle size is controlled by using a porous membrane with desired hole sizes, and, where necessary, by adding energy to the particles of formulation contained in a defined volume of air in an amount sufficient to evaporate bulk media and reduce total particle size.

It is a further object of the invention to provide a method for expressing a polynucleotide preferentially in a specified region of the respiratory tract in vivo.

It is a still further object of the invention to provide a method for generating an immune response in an individual by administering an aerosol comprising a naked or formulated and condensed polynucleotide expression construct encoding an immunogenic peptide to the respiratory tract of the individual.

It is yet another object of the invention to provide a method of transfecting lung cells in vivo by administering an aerosol comprising a naked or formulated and condensed polynucleotide to the respiratory tract of the individual.

DETAILED DESCRIPTION OF THE INVENTION

Before the present methods of generating an aerosol containing a polynucleotide and devices, containers and formulations used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention.

It must be noted that as used herein and in the appended claims, the singular forms "a," "an," and "the" include plural referents unless the context clearly dictates otherwise. Thus, for example, reference to "a formulation" includes mixtures of different formulations, and reference to "the method of delivery" includes reference to equivalent 15 steps and methods known to those skilled in the art, and so forth.

Where a range of values is provided, it is to be understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller range is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All patents publications mentioned herein are incorporated herein by reference.

Definitions

The terms "diameter", "particle diameter", "particle size" and the like are used interchangeably herein to refer to particle size as given in the "aerodynamic" size of the particle. The aerodynamic diameter is a measurement of a particle of unit density that has the same terminal sedimentation velocity in air under normal atmospheric conditions as the particle in question. This is pointed out in that it is difficult to accurately measure the diameter of small particles using current technology and the shape of such small particles may be continually changing. Thus, the diameter of one particle of material of a given density will be said to have the same diameter as another particle of the same material if the two particles have the same terminal sedimentation velocity in air under the same conditions. In connection with the present invention, when targeting the deep lung, it is important to have particles which do not have too large a diameter so that the particles can be inhaled deeply into the lungs and thereby deposited on lung tissue and transferred into the patient's circulatory system. It is equally important not to have particles which are too small in that such particles would be inhaled into the lungs and then exhaled without depositing on the lung tissue in the same manner that particles of smoke can be inhaled and exhaled with only a small amount of the particles being deposited on the lung tissue.

The term "therapeutic polynucleotide", as used herein, intends any polynucleotide which expresses a protein, polynucleotide, antigen, or the like, which is used in the treatment or prevention of any disease, disorder, or condition, or the prevention or treatment of the symptoms of any disease or disorder, for example for vaccination, for the treatment of diseases such as emphysema, cystic fibrosis, and lung cancer; for the expression and systemic delivery of proteins; or, where the therapeutic polynucleotide encodes an antisense or ribozyme polynucleotide, for inhibiting expression of an endogenous polynucleotide.

The term "polynucleotide" or "nucleic acid", as used herein, refers to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups, or modified or substituted sugar or phosphate groups. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides can be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

By "naked" polynucleotide, nucleic acid, DNA sequence and the like is meant a polynucleotide that is not contained within a viral particle, bacterial cell, nonviral (liposomal) carrier or other encapsulating means that facilitates delivery of nucleic acid into the cytoplasm of the target cell. Naked nucleic acid can be associated with means for facilitating delivery of the nucleic acid to the site of the target cell (e.g., means that facilitate travel into the target cell of the nucleic acid, protect the nucleic acid from degradation, and/or serve to penetrate mucus) and/or to the surface of the target epithelial cell.

The term "condensed" polynucleotide, nucleic acid, DNA sequence and the like refers to a polynucleotide which has been mixed with a condensing agent.

The term "condensing agent" or the like refers to a compound or protein that causes a polynucleotide to form condensed particles, and can alter the polynucleotides structure so that it occupies a smaller volume. Ideally, particles of a diameter of 20–50 nm are generated. Condensation is monitored and defined by the resulting zeta potential of the particles which is ideally in the neutral or slightly positive mV range (0–30 mV). Furthermore, condensed polynucleotides are protected from degradation by DNAse I. Ideally strands of DNA several hundreds nms are condensed to particles of 20–50 nm. However, it should be noted that the beneficial effect of condensing agents on delivery occurs even with polynucleotides that are much shorter, including oligonucleotides, and does not result in a measurable change in volume. Suitable condensing agents include polyamines such as spermine, spermidine and putrescine, poly-lysine, poly-ethyleneimine (PEI), polycations, and proteins such as protamine sulfate (Gao and Huang, *Biochem.* 35:1027–1036, 1996; Sorgi et al., *Gene Therapy* 4:961–968, 1997). Such compounds may be isolated from natural sources where polynucleotides exist in a condensed state, for example from sperm cells, or may be chemically synthesized.

The term "bulk medium" or "dispersion liquid" or "solvent" shall mean a liquid or dispersed, flowable, pharmaceutically acceptable excipient material which an active ingredient such as a polynucleotide is mixed with, suspended or dissolved in. The terms "carrier" and "delivery vehicle", used interchangeable herein, shall mean the material which forms the particle that contains the polynucleotide being administered, along with other excipients, including bulk media, required for the safe and efficacious action of the polynucleotide ("agent"). Delivery vehicles are described in more detail below. These carriers may be dissolved, dispersed or suspended in bulk media such as water, ethanol, saline solutions and mixtures thereof. Other bulk media can also be used provided that they can be formulated to create a suitable aerosol and do not adversely affect the active component or human lung tissue. Useful bulk media do not adversely interact with the polynucleotide or viral envelope and have properties which allow for the formation of aerosolized particles preferably particles having a diameter in the range of 1.0 to 75 microns when a formulation comprising the bulk media and active ingredient is forced through pores having a diameter of 0.5 to 25 microns.

The term "formulation" is used to describe any mixture, solution, suspension or the like which contains a polynucleotide and has physical properties such that when the formulation is moved through a porous membrane, the formulation is aerosolized into particles which can be inhaled into the lungs of a patient. The active ingredient may be any pharmaceutically acceptable polynucleotide, and the formulation may include bulk media as described above. Formulations are preferably solutions or suspensions, and can include a low boiling point propellant.

The term "liquid formulation" is used herein to describe any polynucleotide by itself or with a pharmaceutically acceptable carrier in flowable liquid form and preferably having a viscosity and other characteristics such that the formulation is aerosolized into particles which are inhaled into the lungs of a patient after the formulation is moved through a porous membrane of the invention. Such formulations are preferably solutions, e.g. aqueous solutions, ethanolic solutions, aqueous/ethanolic solutions, saline solutions and colloidal suspensions. Formulations can be solutions or suspensions of polynucleotide in any fluid including fluids in the form of a low boiling point propellant.

The term "formulation" is used to encompass the term "liquid formulation" and to further include dry powders of a polynucleotide along with excipient materials. Preferred formulations are aqueous solutions of monomeric insulin but include dry powders and dispersions.

The term "substantially" dry shall mean particles of an aerosol which contain less than 10% free water, ethanol or other liquid carrier based on total weight and preferably contains no detectable free liquid carrier.

The terms "aerosol", "aerosol bolus," and the like are used interchangeably herein to describe a volume of air greater than 50 ml and less than 10 liters which has suspended within it particles of a formulation wherein the particles have a diameter in the range of, 10 in some embodiments, about 1 to about 3 microns, in other embodiments about 4 to about 6 microns, and other embodiments about 6 to about 10 microns, and preferably the total volume of formulation is from 5 µl to 10,000 µl.

The terms "air", "particle free air", "aerosol free air," and the like, are used interchangeably herein to describe a volume of air which is substantially free of other material and, in particular, free of particles intentionally added such as particles of formulation. The terms means that the air does not include particles of formulation which have been intentionally added but is not intended to imply that the normal surrounding air has been filtered or treated to remove all particles although filtering can take place.

The term "inspiratory flow rate" shall mean a value of air flow rate measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, calculated and/or measured volume of air passing a given point into the lungs of a patient assuming atmospheric pressure ±5% and a temperature in the range of 10° C. to 40° C.

The term "inhaling maximally" shall mean that the patient makes a maximal effort to inhale air into the lungs.

The term "inspiratory flow profile" shall be interpreted to mean data calculated in one or more events measuring inspiratory flow and cumulative volume, which profile can be used to determine a point within a patient's inspiratory cycle which is preferred for the release of aerosol to be delivered to a patient. The point within the inspiratory cycle where aerosolized polynucleotide is released may be based on a point within the inspiratory cycle likely to result in the maximum delivery of polynucleotide and/or based on a point in the cycle most likely to result in the delivery of a reproducible amount of polynucleotide to the patient at each release of polynucleotide. Repeatability of the amount delivered is the primary criterion and maximizing the amount delivered is an important but secondary criterion. Thus, a large number of different aerosolized polynucleotide release points might be selected and provide for repeatability in dosing provided the selected point is again selected for subsequent releases. To insure maximum polynucleotide delivery the point is selected within given parameters.

The term "measuring" describes an event whereby either the inspiratory flow rate or inspiratory volume of the patient is measured (via electronic sensors or by mechanical means) in order to determine an optimal point in the inspiratory cycle at which to release aerosolized polynucleotide. An actual measurement of both rate and volume may be made or the rate can be directly measured and the volume calculated based on the measured rate. It is also preferable to continue measuring inspiratory flow during and after delivery of aerosolized polynucleotide and to record inspiratory flow rate and volume before, during and after the release of polynucleotide. Such reading makes it possible to determine if the polynucleotide was properly delivered to the patient.

The term "total lung capacity" is a term which defines the total volume of all air spaces in the lungs of an individual when the lungs of the individual are fully inflated.

The term "residual volume" means the amount of air remaining in the lungs after an individual has fully exhaled.

The term "vital capacity" is the difference between total lung capacity and residual volume.

The terms "region" and "regions of the respiratory tract" are used interchangeably herein to refer to an area or region of the respiratory tract which is based on an approximated model of the lung.

The terms "upper airways", "upper region", "upper respiratory tract" and the like are used interchangeably herein to define an area of the respiratory system which includes the oropharyngeal region and trachea. This area is the first area which air enters the respiratory tract upon inhalation.

The terms "intermediate region", "central airways", "conducting airways", "intermediate area", "bronchial airways" and the like are used interchangeably herein to refer to a region of the respiratory system which during normal breathing substantially remove particles larger than 3 microns in diameter. They are the conductive airways that also clean particles from the lung using mucosal clearance mechanism. Upon inhalation the air passes through the upper region into the intermediate region. In general, if gases are not exchanged in the intermediate region and it is desirable to deliver respiratory agents to this region to treat respiratory diseases such as asthma.

The terms "peripheral region", "outer region", "deep lung", "pulmonary region", "respiratory zone", "alveolated region", "peripheral area" and the like are used interchangeably herein to define a region of the respiratory system where gas exchange occurs between the lungs and the circulatory system—oxygen enters the blood and carbon dioxide leaves the blood.

The terms "alveolar sac", "alveolus" and the like refer to components in the pulmonary region of the lung which are approximately 300 microns in diameter where gas exchange occurs between the air in the lungs and the circulatory system.

The term "gas exchange" refers to the process of supplying the circulatory system with oxygen from air inhaled into the lungs and clearing carbon dioxide from the circulatory system.

The term "dosing event" shall be interpreted to mean the administration of formulation to a patient in need thereof (e.g., inhaling aerosolized particles into the lung) which event may encompass one or more releases of formulation from a dispensing device over a period of time of 1 hour or less, preferably 5 minutes or less, and more preferably 1 minute or less, during which period multiple inhalations may be made by the patient and multiple doses of respiratory agent may be released and inhaled. A dosing event shall involve the administration of formulation to the patient in an amount of about 5 µl to about 10,000 µl in a single dosing event which may involve the release of from about 5 µl to about 10,000 µl of formulation from the device. In that the agent is dissolved or dispersed in a carrier to form the formulation the amount of formulation delivered may be very small and will vary with the concentration of active ingredient in the carrier.

The term "velocity of the agent" or "velocity of particles" shall mean the average speed of particles of formulation moving from a release point such as a porous membrane or a valve toward a patient's respiratory tract. In a preferred embodiment the velocity of the particles is zero or substantially zero (relative to airflow) in the absence of flow created by patient inhalation.

The term "substantially dry" shall mean that particles of formulation include an amount of carrier (e.g., water or ethanol) which is equal to (in weight) or less than the amount of agent in the particle, more preferably it means free or unbound water is not present.

The terms "particles", "aerosolized particles" and "aerosolized particles of formulation" shall mean particles of formulation comprising a polynucleotide and usually a delivery vehicle, which particles are formed upon forcing the formulation through a nozzle which nozzle is preferably in the form of a flexible porous membrane. The particles have a size which is sufficiently small such that when the particles are formed they remain suspended in the air for a sufficient amount of time such that they can be administered to a patient. Preferably, the particles have a size in the range of 0.5 micron to about 75 microns, in some embodiments about 1 to about 3 microns, in other embodiments about 4 to about 6 microns, in still other embodiments about 7 to about 10 microns, having been created by being forced through the pores of a flexible porous membrane which pores have a diameter in the range of about 0.25 micron to about 6.0 microns (note that a pore with a diameter of 4.0 will produce a particle with a diameter of 1–3 times the pore size which particle can be reduced to any size (e.g., 3.0 microns or less) via evaporation—the pores being present on the membrane in an amount of about ten to 10,000 pores over an area in size of from about 1 sq. millimeter to about 1 sq. centimeter).

By "transformation" is meant a permanent or transient genetic change induced in a cell following incorporation of new genetic material (i.e., exogenous to the cell): Where the cell is a mammalian cell, a permanent genetic change is generally achieved by introduction of a polynucleotide, followed by incorporation into the genome of the cell.

By "transfection" is meant the introduction of a polynucleotide into a cell. "Transformation" and "transfection" are used interchangeably herein.

By "transformed cell" is meant a cell having a permanent or transient genetic change introduced by means of recombinant techniques, for example introduction of a DNA molecule.

An "individual" or "subject" or "patient" is a vertebrate, preferably a mammal, usually a human. Mammals include, but are not limited to, farm animals, sport animals, and pets.

An "effective amount" is an amount sufficient to effect beneficial or desired clinical results. An effective amount can be administered in one or more administrations. For the purposes of this invention, in the context of treating a disease state or a condition, an effective amount of a polynucleotide is an amount that is sufficient to palliate, ameliorate, stabilize, reverse, slow or delay the progression of a disease state or a condition being treated. In the context of inducing an immune response, an effective amount of a polynucleotide is an amount that is sufficient to elicit a measurable immune response to an antigen encoded thereby.

As used herein, the terms "treatment", "treating", and the like are used hereinto generally intend obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease of a mammal, particularly a human, and includes:

(a) preventing the disease from occurring in a subject which may be predisposed to the disease but has not yet been diagnosed as having the disease;

(b) inhibiting the disease, i.e., arresting its development; or (c) relieving the disease, i.e., causing regression of the disease The invention provides methods for delivery of an aerosolized formulation of a polynucleotide preferentially to a specified (targeted) area of the respiratory tract of a patient, preferably in a controlled and reproducible manner.

The methods of the present invention are particularly useful with respect to the delivery of a polynucleotide which alters the function of a cell in the targeted region of the respiratory tract. For example, it is possible to create formulations containing a polynucleotide which comprises a gene construct which, when expressed, produces a protein. This protein may be one which the patient is in need of, or it may stimulate an immune response so that the patient is thereby vaccinated. The protein may also be one that induces immunological tolerance, or which produces an enzyme which digests unwanted mucus comprised, in part, of DNA. The protein may also be one that provides a detectable signal, and is thus useful in diagnostic methods.

In some embodiments, polynucleotides are contained within, or associated with, non-viral delivery vehicles. In some of these embodiments, the polynucleotide is delivered naked or formulated and condensed with a carrier. In other embodiments, the polynucleotide is associated with (complexed with) an artificial viral envelope. It is not desirable, in some cases, to deliver the genetic material to the outer-most areas of the lungs where gas transfer takes place. By adjusting various parameters, particularly particle size, but also optionally particle density, inspiratory flow rate, the inspired volume when the aerosol "bolus" is delivered, and the total volume inhaled, specific locations within the respiratory tract, may be targeted. Thus, by methods described herein, it is possible to deliver the genetic material to the desired region(s) of the respiratory tract. When the genetic material is brought into contact with the mucous membranes of the central regions of the lungs or the peripheral gas exchange areas of the lungs or pulmonary macrophages and other cells of the respiratory tract, the material migrates into cells where it is expressed and thereafter the product of the expression delivered to the patient. Alternatively, the polynucleotides, with or without the vehicles, can migrate into the lymph or blood circulation to target other sites in the body.

Methods of Delivering an Aerosolized Polynucleotide Preferentially to a Specified Region of a Respiratory Tract The present invention provides methods of delivering an aerosolized polynucleotide (also referred to herein as "agent") preferentially to a specified region of a mammalian respiratory tract. The methods are useful to deliver polynucleotides, in particular therapeutic polynucleotides, to treat, for example, conditions or disorders which are associated with a particular region of the respiratory tract. The polynucleotides can be delivered locally to sites within the respiratory tract, or can be delivered to a region of the respiratory tract such that they are taken up by the circulatory system, thereby delivering the polynucleotides systemically. In the methods of the present invention, the primary means of achieving delivery preferentially to specified regions of the respiratory tract is by controlling the size of the aerosolized, polynucleotide-containing particles.

The methods of the invention can be used to treat a variety of disorders of the respiratory tract, including, but not limited to, cystic fibrosis, α1-antitrypsin deficiency, adult respiratory distress syndrome, infant respiratory distress syndrome, emphysema, a bacterial, viral, or fungal infection of the respiratory tract, asthma, lung cancer, chronic bronchitis, and pneumonia. The methods are also useful to deliver polynucleotides systemically via the lung, for production of polypeptides, antisense polynucleotides, or ribozymes.

Figure 2:
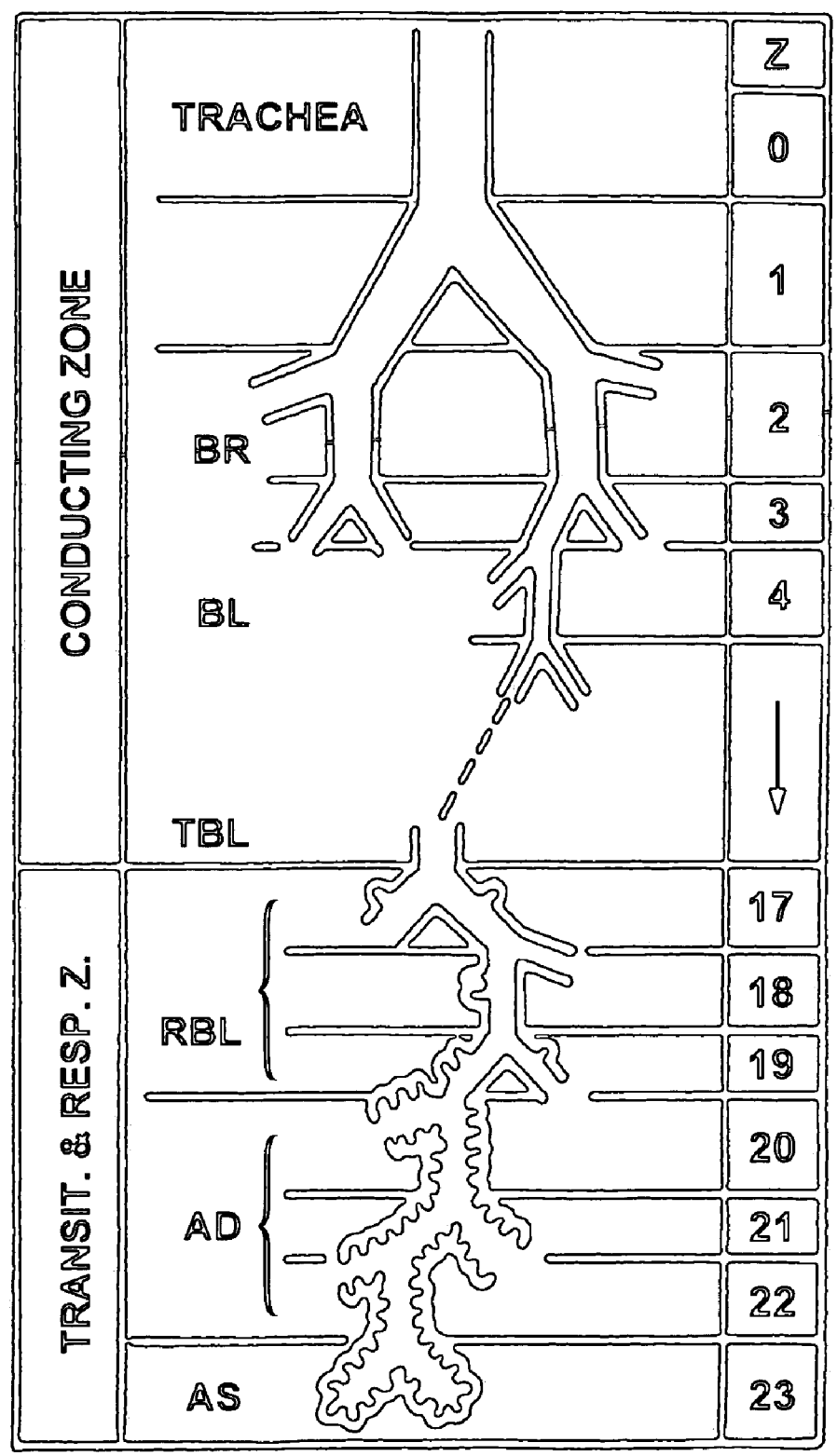
FIG. 2 is a schematic view of a human lung branching pattern.
Figure 3:
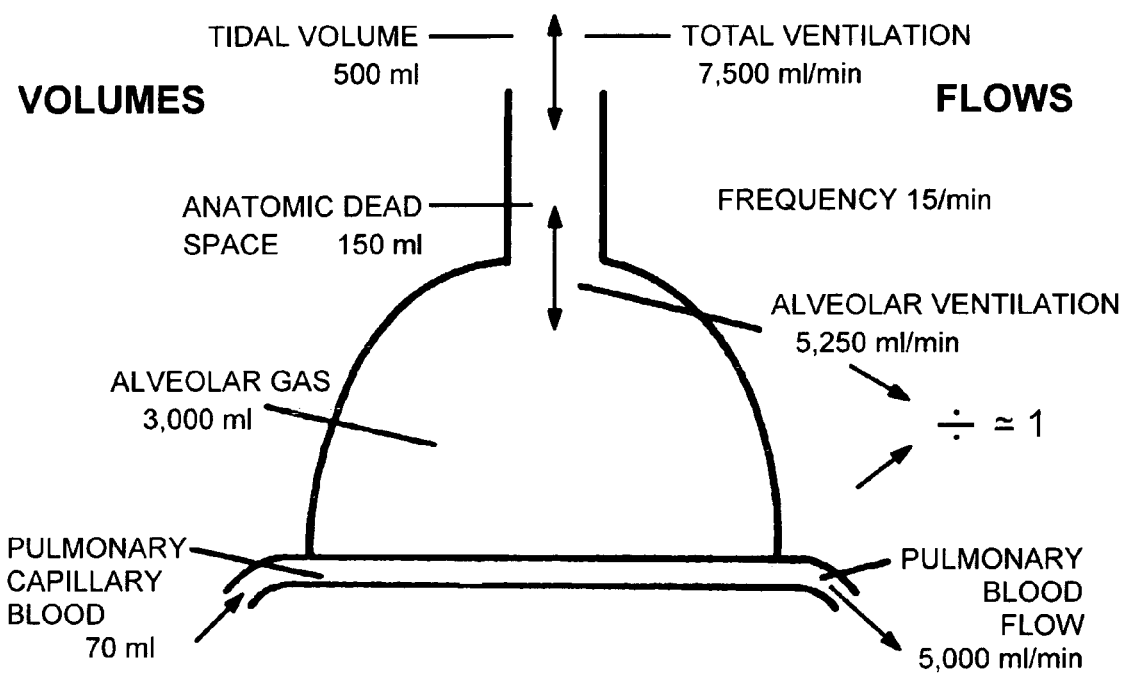
FIG. 3 is a schematic view showing the volumes in particular areas of a human lung.

Methods of the present invention for delivering a polynucleotide preferentially to a specified region of a respiratory tract generally involve aerosolizing a formulation comprising a polynucleotide, thereby forming a population of aerosolized particles, a proportion of which contain the polynucleotide to be delivered, wherein the aerosolized particles have an aerodynamic diameter related to the diameter of airways in an area of the respiratory tract; and administering the aerosolized particles to the respiratory tract (i.e., inhaling the aerosolized particles into the respiratory tract) of the subject, wherein the aerodynamic diameter of the particles targets the particles to the region of the respiratory tract being targeted (i.e., the specified region). For reference, FIGS. 2 and 3 are provided, which present a schematic view of a human lung branching pattern, and a schematic view showing the volumes in particular areas of a human lung, respectively. Thus, aerosolized particles having a size (aerodynamic diameter) in the range of about 1 μm to about 3 μm are preferentially delivered to the alveoli; aerosolized particles having a size in the range of about 4 μm to about 6 μm are preferentially delivered to the central airways; and aerosolized particles having a size in the range of about 7 μm to about 10 μm are preferentially delivered to the upper airways. In some embodiments, the polynucleotide formulation is repeatedly aerosolized into the respiratory tract at an inspiratory flow rate and in an inspiratory volume which are adjusted to the subject's breathing patterns, as described more fully below.

The polynucleotides delivered in the aerosolized particles to the respiratory tract enter a cell of the respiratory tract, and thereafter are expressed, i.e.; a polynucleotide and/or polypeptide encoded by the delivered polynucleotide is synthesized in the cell, or otherwise carry out their intended function. In some embodiments, the polynucleotide enters the circulatory system of the subject and is expressed systemically. Accordingly, in some embodiments, methods are provided for transforming a cell of the respiratory tract, such as a lung cell or other cell of the respiratory tract, preferentially in a targeted region of the respiratory tract, wherein the targeted region is related to the diameter of the airways in that region. In other embodiments, methods for transforming a cell other than a lung cell are provided, where the polynucleotide is targeted to the alveoli, and enters the circulation (e.g., blood or lymphatic) and enters, and is expressed in, a non-lung cell of the body. Transformation can result in transient expression of the polynucleotide, or the polynucleotide can be stably integrated into the genome of the lung (or non-lung) cell, resulting in stable transformation of the cell. Transformed lung cells can be isolated from the subject, for example, by bronchoalveolar lavage, and can be cultured in vitro. Other transformed cells, e.g., non-lung cells, can be isolated from body fluids or tissues and cultured in vitro.

The methods of the present invention are intended for delivery of aerosolized polynucleotides to the respiratory tract of a mammal, including, but not limited to, a human.

The methods provide for "preferential delivery" of aerosolized polynucleotides to specified areas of a mammalian respiratory tract, i.e., at least about 50% to about 60%, more preferably at least about 60% to about 70%, more preferably at least about 70% to about 80%, even more preferably at least about 80% to about 90% or more of a given population of aerosolized particles containing polynucleotide(s) is delivered to the specified area ("target region", or "target location") of the respiratory tract. The remainder of the particles are either not delivered or are delivered to another region of the respiratory tract. The specified area of the respiratory tract to which the particles are delivered is determined by the particle size, as described below. The aerosolized polynucleotides are delivered to a specified region of the respiratory tract, and, preferably, enter a cell in that region. In the case of systemic delivery of a polynucleotide via the alveoli, a polynucleotide can enter a cell in the body other than a lung cell and be expressed therein. Once inside a cell, a polynucleotide and/or polypeptide encoded by the delivered polynucleotide is synthesized. At least about 1%, preferably at least about 10%, more preferably at least about 25%, more preferably at least about 50%, more preferably at least about 75%, even more preferably at least about 90% or more, of the polynucleotides administered to the subject is delivered into the cell or cells of the desired target location, or to a non-lung cell in the case of systemic delivery.

Whether a given population of aerosolized, polynucleotide-containing particles has been delivered preferentially to a specified region of the respiratory tract, and expressed in a cell in the specified region, or in a cell elsewhere in the body, can be readily determined by those skilled in the art using a variety of known methods, including, but not limited to, detecting the polynucleotide itself, or a protein or polynucleotide product encoded by the polynucleotide in a lung biopsy obtained by scraping techniques, use of endoscopes or bronchoscopes, and the like, or a lavage sample, or, in the case of systemic expression, serum or other biological fluid or tissue sample. Methods for detecting polynucleotides and polypeptides in biological samples have been amply described in standard molecular biology and immunology protocols texts including, for example, *Current Protocols in Molecular Biology*, F. M. Ausubel, et al., Eds. (1987, and updates); Harlow et al., *Antibodies: A laboratory manual*, (Cold Spring Harbor, N.Y., 1988); *PCR: The Polymerase Chain Reaction*, Mullis et al., eds. (1994); and *Current Protocols in Immunology*, Coligan et al., eds., 1991.

Detection of a protein product in a biological sample can be achieved by any known means, including, but not limited to, immunoassays, such as "Western" blots, immunoprecipitation, and enzyme-linked immunosorbent assays (ELISA); and enzyme 10 assays (e.g., for detecting an enzyme-encoding reporter gene). Where the polynucleotide is one that comprises a reporter gene, i.e., on that encodes a protein capable of generating a detectable signal, including, but not limited to, a green fluorescent protein, luciferase, and β-galactosidase, detection can be conducted by conventional methods, including, but not limited to, detection, as appropriate, of a fluorescent, bioluminescent, or chromogenic signal. Functional assays can also be conducted to assess a functional property of a polypeptide encoded by a polynucleotide. For example, chloride conductance in a cell transformed with a polynucleotide encoding functional cystic fibrosis transmembrane conductance regulator (CFTR) can be measured by methods known in the art. Enzyme activity of a polypeptide can be assayed, for example, in the case of a polynucleotide which encodes an enzyme.

Detection of a polynucleotide or a polynucleotide product can be achieved by any known means, including, but not limited to, a polymerase chain reaction, in situ hybridization, RNA blots, and DNA blots. For example, mRNA can be isolated by the acid guanidinium thiocyanate:phenol:chloroform extraction method (Chomczynski et al., (1987) *Anal Biochem* 162:156–159) from an appropriate biological sample to determine expression levels by Northern blots. Radioactive or enzymatically labeled probes can be used to detect mRNA in situ. If desired, the mRNA can be reverse transcribed and amplified, for example, by a polymerase chain reaction, and the sample can be probed using conventional methods. Standard procedures can be employed, with samples sectioned as frozen material. Sections are hybridized with antisense probe, using sense probe as a control. After appropriate washing, bound radioactive probes are detected by autoradiography or enzymatically labeled probes are detected through reaction with the appropriate chromogenic substrates.

Aerosolized Particle Size

One aspect of the invention involves manipulating the particle size in order to treat (target) particular areas of the respiratory tract. By creating aerosolized particles which have a relatively narrow range of size, it is possible to further increase the efficiency of the agent delivery and improve the reproducibility of the dosing.

For a given population of aerosolized particles comprising polynucleotides, a population of aerosolized particles has a certain aerodynamic size range, i.e., the mean particle size is within the specified range and at least about 50%, more preferably at least about 60%, more preferably at least about 70%, even more preferably at least about 80%, even more preferably at least about 90% or more of the particles being delivered to a subject have a particle diameter which is within ±50% of the average particle size. For delivery of an aerosolized polynucleotide preferentially to the alveoli, it is preferable that the particles have a size in the range of about 1 µm to about 3 µm. Accordingly, in some embodiments, the methods of the present invention provide delivery of aerosolized polynucleotides, wherein the mean particle size is in the range of about 1 µm to about 3 µm. When it is desirable to deliver a polynucleotide to the intermediate areas of the lung, it is preferable that the aerosolized particles be within the size range about 4 µm to about 6 µm. Accordingly, in some embodiments, the methods of the present invention provide delivery of aerosolized polynucleotides, wherein the mean particle size is in the range of about 4 µm to about 6 µm. When it is desirable to treat the upper areas of the lung, larger particle sizes are used and the particle size is adjusted to a larger size, e.g., about 7 µm. Accordingly, in some embodiments, the methods of the present invention provide delivery of aerosolized polynucleotides, wherein the mean particle size is in the range of 5 to 10 µm, generally about 7 µm. In some instances, it is desirable to treat both intermediate and upper areas of the respiratory tract simultaneously and to deliver aerosolized agent wherein the particle size is distributed over two different ranges. Accordingly, in some embodiments, the methods of the present invention provide delivery of aerosolized polynucleotides to the upper and intermediate respiratory tract, wherein the mean particle size is in the range of 1 to 10 µm, generally about 4 to 7 µm.

To achieve aerosolized particles of a particular size range, various parameters can be modified, including, but not limited to, pore size of the aerosolization membrane; temperature of aerosolization; extrusion velocity; ambient humidity; the concentration, surface tension, and viscosity of the formulation; and vibration frequency.

Aerosol particle size can be adjusted by adjusting the size of the pores of the membrane. In general, for delivery to the respiratory tract, the aerosol is created by forcing the drug formulation through a nozzle comprised of a porous membrane having pores in the range of about 0.25 to 6.0 microns in size, preferably 0.5 to 5.0 microns. When the pores have this size the droplets that are formed will have a diameter about twice the diameter of the pore size. In order to ensure that the low resistance filter has the same or less flow resistance as the nozzle, the pore size and pore density of the filter should be adjusted as necessary with adjustments in pore size and pore density of the nozzle's porous membrane.

Particle size can also be adjusted by adding heat to evaporate carrier. From the period of time from the formation of the aerosolized particles until the particles actually contact the lung surface, the size of the particles is subject to change due to increases or decrease in the amount of water in the formulation due to the relative humidity within the surrounding atmosphere. In order to obtain consistency in terms of the size of particles delivered to the patient regardless of the surrounding atmosphere, it may be desirable to include a component within the aerosol delivery device that adds energy to the surrounding atmosphere (heats the atmosphere) and thereby minimizes the effect of high humidity conditions and reduces the particle size to a minimum consistent size. When it is desirable to decrease particle size by heating, a heating element is used. The amount of heat added to the air is about 20 Joules or more, generally about 20 Joules to about 100 Joules, generally about 20 Joules to about 50 Joules per 10 µl of formulation.

Alternatively, water vapor can be added to the surrounding atmosphere of the aerosol so that the particles would always enlarge to a maximum consistent size.

Particle size can also be adjusted by the use of a vibration device which provides, for example, a vibration frequency in the range of about 800 to about 4000 kilohertz. Vibration devices useful in the delivery devices of the present invention are described in U.S. Pat. Nos. 5,497,763; 5,819,726; 5,906,202; and 5,522,385, each of which is incorporated herein by reference.

Delivery Devices

A variety of devices suitable for use in delivery methods of the invention are known in the art. In general, any device which allows one to control aerodynamic particle size can be used in the methods of the invention. These devices include, but are not limited to, metered-dose inhalers, dry powder inhalers, and nebulizers. Generally, the aerosol is generated by a aerosolizer system which delivers the aerosol through a mouthpiece, facemask, etc., from which the subject can draw the aerosol into the respiratory tract. Examples of suitable devices are found in U.S. Pat. Nos. 5,404,871; 5,450,336; 5,718,222; 5,823,178; 5,829,435; and 5,906,202; and in Schuster et al. (1997) *Pharm. Res.* 14:354–357. Other aerosolizing devices have been described in the art, and can be used in the methods described herein, provided that particles having a desired size range can be produced.

By quantitatively measuring the inspiratory flow rate and volume during the subject's inspiratory maneuver while breathing through the aerosolization system, an optimum point for the delivery of a bolus of aersolized polynucleotide can be determined. Accordingly, in some embodiments, the method comprises (a) determining an inspiratory volume of the subject; (b) aerosolizing a formulation comprising a polynucleotide, thereby forming aerosolized particles having an aerodynamic diameter related to the diameter of airways in an area of a respiratory tract of the subject; (c) inhaling the aerosolized particles into the respiratory tract of the subject, wherein the aerodynamic size of the particles is related to the diameter of airways in the specified region of the respiratory tract; and (d) repeatedly aerosolizing the polynucleotide formulation at the same determined inspiratory volume. In some of these embodiments, the inspiratory volume of the subject is determined by coaching the subject to inhale a given amount. In other embodiments, the inspiratory volume of the subject is determined by measuring airflow electronically.

In some embodiments, the device is one that allows repeated delivery of the aerosolized particles to the respiratory tract of a subject, and that adjusts various parameters of delivery in response to the subject's breathing patterns (i.e., inspiratory flow rate and volume). In order to target an area of the lung particle size is adjusted by adjusting the size of the pores in the porous membrane through which the formulation is moved to create an aerosol and by adding heat if necessary to evaporate liquid carrier away from aerosolized particles formed. In addition to (1) adjusting particle size, uniform deposition of particles on lung tissue is obtained by (2) adjusting the volume of aerosol and aerosol free air released, and (3) releasing at a desired point in the patient's inspiratory flow cycle. To determine the amounts of aerosol and aerosol free air to be released, measurements of total lung capacity are made and used based on where in the lung the respiratory drug is to be delivered. To determine a release point, a patient's inspiratory flow rate is measured and a determination is made of a typical and preferred rate and volume for the release of aerosol. To obtain repeatability in dosing, the aerosol is repeatedly released at the same rate and volume as determined in real time, and volume of the aerosolized air is maintained constant as is the volume of aerosol free air preceding or following the aerosolized bolus. Thus, the method involves measuring for, determining and/or calculating a firing point or aerosol release decision based on instantaneously (or real time) calculated, measured and/or determined inspiratory flow rate and inspiratory volume points as well as the patient's lung capacity and the area of the lung to be medicated. The amount of formulation delivered is maximized relative to the amount released when the drug is released at a rate of from about 0.10 to about 2.0 liters/second, and a volume of about 0.5 to about 2.0 liters. Parameters such as rate, volume, and particle size of the aerosolized formulation are adjusted to obtain repeatable dosing of the maximum amount of drug to the desired area of the lung. Lung function is measured and use parameters are adjusted in order to improve lung function. The volume 1′ 5 of the aerosol and aerosol free air released is adjusted based on the patient's lung volume and the areas of the lung to be treated.

In one embodiment, the delivery device useful for administering polynucleotides is one described in commonly assigned U.S. Pat. No. 5,906,202, which is herein incorporated by reference. The release point of the device during inspiration is automatically determined either mechanically or, more preferably calculated by a microprocessor which receives data from an electronic sensor. A number of parameters are measured which may include total lung capacity, inspiratory flow rate and inspiratory volume in order to determine how much aerosol and aerosol-free air is to be released, and when in the inspiratory cycle it should be released. The device is loaded with a cassette comprised of an outer housing which holds a package of individual collapsible containers of formulation comprising a carrier with a polynucleotide, optionally included in an artificial viral envelope and preferably condensed. Actuation of the device forces the formulation through a porous membrane of the container which membrane has pores having a diameter in the range of about 0.5 to 25 microns.

To direct aerosolized formulation to a specific area of the lung, the particle size is controlled. In addition, the volume of a delivered aerosol bolus can be controlled, as can the volume of aerosol free air preceding and/or following the aerosol bolus. By controlling the volume of aerosol and aerosol free air released, and the point of release it is possible to regulate how far into the lung aerosol formulation is drawn. The device is also capable of preventing further inhalation after a given volume has been inhaled. By using such a procedure, an inhaled bolus of aerosol can be delivered to a desired point in the lungs and allowed to settle there.

In a particular embodiment of the method of the invention, the patient is instructed to carry out the following breathing maneuvers. (1) The patient exhales fully through the device so that only residual air is left in the respiratory system. (2) The patient inhales to maximum volume and during the inhalation the patient is instructed to watch lights on the device which will prompt the patient towards the correct rate of inhalation by signaling via flashing red light when inhalation is too fast, not lighting at all when too slow and providing a constant green light when the correct rate is obtained. (3) Exhaling again through the device until only residual air is left within the respiratory system. (4) Inhale again to the point where the device stops further inhalation or prompts the patient to stop the inhalation after the predetermined inhaled volume has been reached which is done while watching the lights (or having a sound) in order to obtain the correct rate of inhalation. Maneuvers (1)–(4) will individually calibrate the device for the particular patient at that point in time. Steps 1–4 are repeated to recalibrate at any given later dosing event in that a patient's lung function may change over time. Within step (2) the inhaled volume is measured and used to calculate an optimal point for release of aerosolized air during step (4).

In some embodiments, a device suitable for use in the methods of the invention provides a number of features which make it possible to direct any desired volume of aerosol to an area and achieve controlled and repeatable delivery to deposit a polynucleotide containing the same. Specifically, for a particular patient population, disease, age, sex and therapeutic or diagnostic polynucleotide, one may need to adjust:

(1) the specific volumes of aerosol and particle free air with consideration to total lung capacity in order to target agent delivery to a specific region of the lungs;

(2) the release point within a patient's inspiratory volume, the release point being as necessary from 0.5 liters or greater up to the patient's vital capacity volume;

(3) the release point within a patient's inspiratory flow rate inside a range of about 0.10 to about 4.0 liters/second preferably about 0.2 to about 3.0 liters per sec.;

(4) particle size for topical pulmonary delivery in a range of about 0.5 to 5 microns, preferably 1.0 to 3.0 microns;

(5) the amount of heat added to the air to be from 0 Joules to about 100 Joules and preferably about 20 Joules to about 50 Joules per 10 µl of formulation;

(6) the relative volume of air added by patient inhalation per 10 µl of formulation is about 100 ml to about 10 liters and preferably about 200 ml to about 5 liters;

(7) the rate of vibration of the porous membrane from 575 to 32,000 kilohertz, preferably 1,000 to 17,000 and more preferably 2,000 to 4,000 kilohertz;

(8) pore size to a range of about 0.25 to about 6.0 microns in diameter preferably 0.5 to 3 microns which is the size of the diameter of the exit opening it being noted that the pore preferably has a conical configuration with the entrance opening being 2 to 20 times the diameter of the exit opening;

(9) viscosity of the formulation to a range of from about 25% to 1,000% of the viscosity of water;

(10) extrusion pressure to a range of about 50 to 1000 psi and preferably 100 to 700 psi;

(11) ambient temperature to 15° C. to 30° C. and ambient pressure between 1 atmosphere and 75% of 1 atmosphere;

(12) the ratio of bulk media to agent in a formulation to be consistent;

(13) the solubility of agent in bulk media to use highly soluble agents or to use a fine (nanometer size range) dispersion of agent in bulk media;

(14) the desiccator to maximize removal of water, or other carrier, from air;

(15) the shape of the pore opening to be circular in diameter and conical in cross-section with the ratio of the diameter of the small to large end of the cone being about ½ to $\frac{1}{20}$, and the shape of the porous membrane to an elongated oval;

(16) the thickness of the membrane to 5 to 200 microns; preferably 10–50 microns and a tensile strength of over 5,000 psi;

(17) the membrane to have a convex shape or to be flexible so that it protrudes outward in a convex shape preferably beyond the flow boundary layer when formulation is forced through it; and

(18) the firing point to be at substantially the same point at each release for the parameters (1–17), i.e., each release of agent is at substantially the same point so as to obtain repeatability of dosing.

The formulation is automatically aerosolized at a point in the respiratory cycle after receipt of a signal from a microprocessor programmed to commence aerosol delivery when a signal is received from a monitoring device such as an airflow rate monitoring device. In some applications, a patient using the device withdraws air from a mouthpiece and the total lung capacity, inspiratory flow rate, as well as the inspiratory volume of the patient, are determined one or more times in a monitoring event which determines the volume of aerosol and particle free air to be inhaled and a preferred point in an inhalation cycle for the release of both the aerosol and the particle free air. Inspiratory flow rate and volume, as well as total lung capacity, are each determined and recorded in one or more monitoring events for a given patient in order to develop an inspiratory flow profile for the patient. The recorded information is analyzed by the microprocessor in order to deduce the timing and volume of aerosol and particle free air to be released into the patient's inspiratory cycle with the preferred volumes and point being calculated based on the most likely volume and point to result in repeatably efficient delivery to a specifically targeted area of the lungs.

The combination of automatic control of the release of aerosols, combined with frequent monitoring events in order to calculate the (1) total lung capacity, (2) volumes to release to treat specific areas, (3) optimal flow rate, and (4) time for the release of an aerosol, combine to provide a repeatable, efficient means of delivering formulation to a particular area of the lungs of a patient. In that aerosolized volume is metered and released automatically and not manually, it can be predictably and repeatedly delivered to any desired area of the lung during a particular dosing event. Because dosing events are preferably preceded by monitoring events, the volume and amount of aerosol released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount, volume, and/or point of release of the aerosol and aerosol free air boluses in a manner calculated to provide for the administration of the same amount of formulation to the same area of the lungs of the patient at each dosing event.

In order to achieve a reproducible therapeutic effect, it may be desirable to release agent at the same inspiratory flow rate and same inspiratory volume point each time agent is delivered to the patient. By picking the same flow rate and same volume point for each release a high degree of repeatability in dosing is obtained. Thus, even if the efficiency is relatively low the patient can be repeatedly dosed at a known inefficient level and still provide the patient with the desired amount of formulation. However, by choosing an inspiratory flow rate within a specific range as well as choosing an inspiratory volume within a specific range, the efficiency of agent delivery can also be increased relative to merely delivering at any flow rate or volume and then returning to that same point for each subsequent release. Some fluctuation with respect to the desired inspiratory flow rate and volume for delivery from patient to patient, as well as from the progress of disease and aging within a patient, is expected. However, it is generally desirable to deliver agent at an inspiratory flow rate in the range of about 0.2 to about 4.0 liters per second, more preferably 0.15 to 3.0 liters per second. Thus, the device is designed to release agent within the preferred range and after release to return to the same point (as closely as possible) for the next release of agent.

With respect to devices suitable for use in the methods of the present invention, the inspiratory volume for agent release is more involved. First, some adjustments may be made based on the patients total lung volume. For purposes of example information is provided here assuming an adult male with a 5 liter total lung volume. In such a situation the patient will have a residual volume of about 1.5 liters and thus a vital capacity of 3.5 liters. The device could then be set to release agent after the patient had inhaled 1.5 liters of particle free air. At this point, the lungs would include 3 liters of particle free air (1.5 residual and 1.5 inhaled) and agent release would begin. The agent release would involve the inhalation of approximately 200 ccm or 0.2 liters of aerosol. The aerosol delivery would be followed immediately by the inhalation of particle free air in a volume which is sufficient to fill the large airways (e.g., airways having a diameter of, for example, 1 mm or more (approximately a volume of 150 ccm) plus a volume sufficient to fill the oropharyngeal volume (approximately 200 ccm). Thus, the aerosol dose of 200 ccm is followed by the inhalation of approximately 350 ccm of particle free air.

At this point, the patient's lungs with a 5 liter volume include 1.5 liters of residual air, 1.5 liters of inhaled particle free air, 0.2 liters of aerosol, and 0.35 liters of additional particle free air for a total of 3.55 liters. At this point the device prevents further inhalation (or signals the patient to stop inhalation) and the patient is in a breath holding mode. The patient is instructed to hold his or her breath for a given period of time which is preferably timed by the inhalation device. At the end of the period the device will provide the patient with an indication that breath may be released so that the patient can continue with normal breathing. By carrying out the maneuver in this manner the 0.2 liter of aerosol is delivered preferentially to the intermediate region of the lung within large (central) bronchial airways.

Polynucleotides Delivered to Specified Regions of the Respiratory Tract Using Methods of the Invention The present invention provides methods of delivering a polynucleotide preferentially to a specified (targeted) region of a mammalian respiratory tract. A variety of different types of polynucleotides can be delivered using the methods of the invention, and the choice of polynucleotide will depend on the area of the respiratory tract being targeted and the desired result. The polynucleotide may be a therapeutic polynucleotide, or one suitable for use in diagnostic methods, such as a polynucleotide which encodes a polypeptide which provides a detectable signal.

Polynucleotides which are contemplated for use in the methods of the invention include expression vectors of viral or non-viral origin, antisense molecules, ribozymes, and the like. In general, the polynucleotides are in vectors capable of being expressed in eukaryotic cells, particularly mammalian cells. A wide variety of such expression vectors are known in the art and can be used in the methods of the present invention. See, for example, *Gene Transfer Vectors for Mammalian Cells*, Miller and Calos, eds. 1987; Ausubel (1987, and updates); and *Molecular Cloning: A Laboratory Manual*, Sambrook et al., eds. 1989. The polynucleotides may be isolated from a host cell, a culture supernatant (for example, from viral particles), may be chemically or enzymatically synthesized, or may be generated by standard molecular biology techniques. The polynucleotide may be composed of DNA, RNA, synthetic nucleotide variants and analogs, or combinations thereof. The polynucleotide may be single stranded, double stranded, circular or linear. The polynucleotide may be condensed with a suitable condensing agent so that it can be delivered intact via aerosolization. Construction of polynucleotides comprising coding regions capable of being expressed in eukaryotic cells is amply described in a variety of standard molecular biology protocols texts, including *Current Protocols in Molecular Biology*, F. M. Ausubel, et al., Eds. (1987, and updates).

Therapeutic polynucleotides within expression constructs include any polynucleotide encoding a protein having a therapeutic effect. Therapeutic polynucleotides contemplated for use in the methods of the invention include, but are not limited to, CFTR; an enzyme, including, but not limited to, a DNAse, inducible nitric oxide synthetase, superoxide dismutase, and catalase; plasminogen activator; α1-antitrypsin; growth factors such as VEGF or an EGF family member, their receptors, thrombopoietin, erythropoietin; cytokines such as GM-CSF, interleukins, tumor necrosis factor; hormones, including insulin, antibodies, or active fragments thereof; for the treatment of lung cancer, tumor suppressor genes such as p53 or BRCA1, genes encoding toxic polypeptides such as ricin and diphtheria toxin, or biologically active derivatives thereof; and genes known to encode peptides having antiviral or antibacterial activity. Also contemplated are polynucleotides which express one or more foreign proteins in the subject, which foreign proteins will stimulate an immune response. Further contemplated are polynucleotides which express one or more proteins which induce immunological tolerance. Also included are polynucleotides encoding polypeptides which provide a detectable signal, including, but not limited to, a green fluorescent protein, luciferase, and β-galactosidase. A given polynucleotide can include both a therapeutic polynucleotide and a nucleotide sequence encoding a protein capable of producing a detectable signal. Nucleotide sequences for a wide variety of polynucleotides are publicly available through a variety of sources, including GenBank databases.

Therapeutic polynucleotides include antisense expression constructs or ribozymes towards genes encoding proteins involved in lung disease, for example for proteolytic enzymes such as elastase or to dominant negative forms of p53, antisense to oncogenes.

Expression constructs generally include a transcriptional control element, typically a promoter, operably linked to the coding region of interest to facilitate expression of the polynucleotide of interest. A variety of promoters are known in the art, including strong promoters active in eukaryotic cells, including a promoter from cytomegalovirus (CMV), mouse mammary tumor virus (MMTV), Rous sarcoma virus (RSV), or adenovirus. Exemplary promoters include the promoter from the immediate early gene of human CMV (Boshart et al., *Cell* 41:521–530, 1985); the promoter from the long terminal repeat (LTR) of RSV (Gorman et al. (1982 *Proc. Natl. Acad. Sci. USA* 79:6777–6781); SV40 early promoter; and the adenovirus major late promoter. Alternatively, the promoter used may be a tissue-specific promoter, a variety of which are known in the art.

Other control sequences operably linked to the polynucleotide of interest can be included. Nucleic acid "control sequences" or "regulatory elements" refer collectively to promoter sequences, ribosome binding sites, polyadenylation signals, transcription termination sequences, upstream regulatory domains, enhancers, and the like, which collectively provide for the transcription and translation of a coding sequence in a eukaryotic cell.

Other components may be included in the vector such as a marker (e.g., an antibiotic resistance gene, such as an ampicillin resistance gene, a gene encoding a green fluorescent protein or a β-galactosidase-encoding gene) to aid in selection and/or visualization of cells containing and/or expressing the construct, an origin of replication for stable replication of the construct in a bacterial cell (preferably, a high copy number origin of replication), a nuclear localization signal, or other elements which facilitate production of the expression construct, the protein encoded thereby, or both. In some embodiments, the polynucleotide will express one or more foreign proteins in the host, which foreign proteins will stimulate an immune response.

Antisense molecules and ribozymes of the invention can be prepared by methods known in the art for the synthesis of RNA molecules, including techniques for chemical oligonucleotide synthesis, e.g., solid phase phosphoramidite chemical synthesis. Alternatively, RNA molecules can be generated by in vitro and in vivo transcription of DNA sequences. Such DNA sequences can be incorporated into a wide variety of vectors with suitable RNA polymerase promoters (e.g., T7 or SP6). Alternatively, antisense expression constructs useful in the constitutive or inducible synthesis of antisense RNA can be introduced into cell lines, cells, or tissues.

RNA molecules can be modified to increase intracellular stability and half-life. Possible modifications include, but are not limited to, the addition of flanking sequences at the 5' and/or 3' ends of the molecule, or the use of phosphorothioate, phosphorodithioate or 2' O-methyl rather than phosphodiesterase linkages within the backbone of the molecule. This concept can be extended in all of these molecules by the inclusion of nontraditional bases such as inosine, queosine and wybutosine as well as acetyl-, methyl-, thio- and similarly modified forms of adenine, cytidine, guanine, thymine, and uridine that are not as easily recognized by endogenous endonucleases.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 95/23225, and Beigelman et al. (1995) *Nucl. Acids Res.* 23:4434–42). Examples of oligonucleotides with catalytic activity are described in WO 9506764. Conjugates of anti-sense oligonucleotides with a metal complex, e.g. terpyridylCu(II), capable of mediating mRNA hydrolysis are described in Bashkin et al. (1995) *Appl. Biochem. Biotechnol.* 54:43–56.

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. The invention contemplates engineered hammerhead motif ribozyme molecules that can specifically and efficiently catalyze endonucleolytic cleavage of targeted sequences.

Specific ribozyme cleavage sites within any potential RNA target are initially identified by scanning the target molecule for ribozyme cleavage sites, which sites include the following sequences, GUA, GUU and GUC. Once identified, short RNA sequences between 15 and 20 ribonucleotides corresponding to a region of the target gene containing the cleavage site can be evaluated for secondary structural features that can render the oligonucleotide inactive. The suitability of candidate targets can also be evaluated by testing accessibility to hybridization with complementary oligonucleotides using ribonuclease protection assays.

A polynucleotide can be isolated from suitable cells or organisms, or may be synthesized either chemically or enzymatically, or may be prepared using standard techniques of molecular biology, or combinations of such techniques may be used. For example, expression constructs may be propagated in a prokaryotic host. Alternatively, viral particles containing the polynucleotide of interest may be isolated from a culture, for example, and the polynucleotides may be isolated therefrom. In vitro replication strategies may be used, for example long PCR, so that a construct can be propagated outside the confines of a host cell (Barnes *Proc. Natl. Acad. Sci. USA* 91:2216–2220, 1994; Cheng et al., *Proc. Natl. Acad. Sci. USA* 91:5695–5699, 1994). Any suitable method by which the polynucleotide of interest can be generated may be used.

The polynucleotides are generally purified so that they are acceptable for their intended use. The term "purified" in this context indicates that the polynucleotide is substantially free, i.e., 90% or greater, of undesired extraneous genetic material and immunogenic substances such as viral coat or host cell proteins, as well as free from toxic or harmful chemical substances. Any suitable technique using reagents of sufficient purity may be used. Purification may be based on charge, density, polarity, solubility, affinity, migration through a matrix or column, and the like. Suitable methods of purification include those found in U.S. Pat. No. 5,561,064.

In general, an isolated, purified viral genome used in accordance with the invention is derived from a naturally-occurring virus which has been genetically altered to render the virus replication-defective and to express a recombinant gene of interest in accordance with the invention. Once the virus delivers its genetic material to a cell, it does not generate additional infectious virus but does introduce exogenous recombinant genes into the cell, preferably operably inserted into the genome of the cell. Alternatively, in some embodiments, a viral genome is replication-competent. In still other embodiments, the viral genome is replication-conditional.

Polynucleotides delivered to specified areas of the respiratory tract using methods of the invention can be delivered in viral or non-viral delivery vehicles. Choice of a particular delivery vehicle may depend on several factors, including whether an immune response to the vehicle is desired, whether, in the case of viral delivery vehicles, the spread of the polynucleotide from cell to cell is desired, etc. A polynucleotide can be delivered as a naked polynucleotide, or associated with ("complexed with") a delivery vehicle. "Associated with", or "complexed with", encompasses both covalent and non-covalent interaction of a polynucleotide with a given delivery vehicle.

Viral Delivery Vehicles

Polynucleotides delivered by the methods of the invention can be associated with viral delivery vehicles. As used herein, a "viral delivery vehicle" intends that the polynucleotide to be delivered is encapsidated in a viral particle.

Numerous viral genomes useful in in vivo transformation and gene therapy are known in the art, or can be readily constructed given the skill and knowledge in the art. Included are replication competent, replication deficient, and replication conditional viruses. Viral vectors include adenovirus, mumps virus, a retrovirus, adeno-associated virus, herpes simplex virus (HSV), cytomegalovirus (CMV), vaccinia virus, and poliovirus, and non-replicative mutants/ variants of the foregoing. In some embodiments, a replication-deficient virus is capable of infecting slowly replicating and/or terminally differentiated cells, since the respiratory tract is primarily composed of these cell types. For example, adenovirus efficiently infects slowly replicating and/or terminally differentiated cells. In some embodiments, the viral genome itself, or a protein on the viral surface, is specific or substantially specific for cells of the targeted cell. A viral genome can be designed to be target cell-specific by inclusion of cell type-specific promoters and/or enhancers operably linked to a gene(s) essential for viral replication.

Where a replication-deficient virus is used as the viral genome, the production of virus particles containing either DNA or RNA corresponding to the polynucleotide of interest can be produced by introducing the viral construct into a recombinant cell line which provides the missing components essential for viral replication and/or production. Preferably, transformation of the recombinant cell line with the recombinant viral genome will not result in production of replication-competent viruses, e.g., by homologous recombination of the viral sequences of the recombinant cell line into the introduced viral genome. Methods for production of replication-deficient viral particles containing a nucleic acid of interest are well known in the art and are described in, for example, Rosenfeld et al., Science 252:431–434, 1991 and Rosenfeld et al., Cell 68:143–155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., J. Virol. 67:2928–2931, 1993; Takeuchi et al., Archiv. Virol., 128:177–183, 1993; Tanabayashi et al., Virol. 187:801–804, 1992; Kawano et al., Virol., 179:857–861, 1990; Elango et al., J. Gen. Virol. 69:2893–28900, 1988.

Non-Viral Delivery Vehicles

The polynucleotide of interest may alternatively be administered using a non-viral delivery vehicles. "Non-viral delivery vehicle" (also referred to herein as "non-viral vector") as used herein is meant to include chemical formulations containing naked or condensed polynucleotides (e.g., a formulation of polynucleotides and cationic compounds (e.g., dextran sulfate)), and naked or condensed polynucleotides mixed with an adjuvant such as a viral particle (i.e., the polynucleotide of interest is not contained within the viral particle, but the transforming formulation is composed of both naked polynucleotides and viral particles (e.g., adenovirus particles) (see, e.g., Curiel et al. 1992 Am. J. Respir. Cell Mol. Biol. 6:247–52)). Thus "non-viral delivery vehicle" can include vectors composed of polynucleotides plus viral particles where the viral particles do not contain the polynucleotide of interest. "Non-viral delivery vehicles" include bacterial plasmids, viral genomes or portions thereof, wherein the polynucleotide to be delivered is not encapsidated or contained within a viral particle, and constructs comprising portions of viral genomes and portions of bacterial plasmids and/or bacteriophages. The term also encompasses natural and synthetic polymers and co-polymers. The term further encompasses lipid-based vehicles. Lipid-based vehicles include cationic liposomes such as disclosed by Felgner et al (U.S. Pat. Nos. 5,264,618 and 5,459,127; PNAS 84:7413–7417, 1987; Annals N.Y. Acad. Sci. 772:126–139, 1995); they may also consist of neutral or negatively charged phospholipids or mixtures thereof including artificial viral envelopes as disclosed by Schreier et al. (U.S. Pat. Nos. 5,252,348 and 5,766,625).

Non-viral delivery vehicles include polymer-based carriers. Polymer-based carriers may include natural and synthetic polymers and co-polymers. Preferably, the polymers are biodegradable, or can be readily eliminated from the subject. Naturally occurring polymers include polypeptides and polysaccharides. Synthetic polymers include, but are not limited to, polylysines, and polyethyleneimines (PEI; Boussif et al., PNAS 92:7297–7301, 1995) which molecules can also serve as condensing agents. These carriers may be dissolved, dispersed or suspended in a dispersion liquid such as water, ethanol, saline solutions and mixtures thereof. A wide variety of synthetic polymers are known in the art and can be used.

"Non-viral delivery vehicles" further include bacteria. The use of various bacteria as delivery vehicles for polynucleotides has been described. Any known bacterium can be used as a delivery vehicle, including, but not limited to non-pathogenic strains of Staphylococcus, Salmonella, and the like.

The polynucleotide to be delivered can be formulated as a DNA- or RNA-liposome complex formulation. Such complexes comprise a mixture of lipids which bind to genetic material (DNA or RNA) by means of cationic charge (electrostatic interaction). Cationic liposomes which may be used in the present invention include 3β-[N—(N',N'-dimethylaminoethane)-carbamoyl]-cholesterol (DC-Chol), 1,2-bis (oleoyloxy-3-trimethylammonio-propane (DOTAP) (see, for example, WO 98/07408), lysinylphosphatidylethanolamine (L-PE), lipopolyamines such as lipospermine, N-(2-hydroxyethyl)-N,N-dimethyl-2,3-bis(dodecyloxy)-1-propanaminium bromide, dimethyl dioctadecyl ammonium bromide (DDAB), dioleoylphosphatidyl ethanolamine (DOPE), dioleoylphosphatidyl choline (DOPC), N(1,2,3-dioleyloxy)propyl-N,N,N-triethylammonium (DOTMA), DOSPA, DMRIE, GL-67, GL-89, Lipofectin, and Lipofectamine (Thiery et al. (1997) Gene Ther. 4:226–237; Felgner et al., Annals N.Y. Acad. Sci. 772:126–139, 1995; Eastman et al., Hum. Gene Ther. 8:765–773, 1997). Polynucleotide/lipid formulations described in U.S. Pat. No. 5,858,784 can also be used in the methods described herein. Many of these lipids are commercially available from, for example, Boehringer-Mannheim, and Avanti Polar Lipids (Birmingham, Ala.). Also encompassed are the cationic phospholipids found in U.S. Pat. Nos. 5,264,618, 5,223,263 and 5,459,127. Other suitable phospholipids which may be used include phosphatidylcholine, phosphatidylserine, phosphatidylethanolamine, sphingomyelin, phosphatidylinositol, and the like. Cholesterol may also be included.

The polynucleotide of interest can be administered using an artificial viral envelope (AVE), either alone or in combination with a condensing agent. Artificial membranes can be prepared, for example, by double detergent dialysis as described in U.S. Pat. Nos. 5,252,348 and 5,766,625; and European Patent No. 555,333 B1. These viral envelopes generally have a cholesterol:phospholipid ratio of about 0.8 to about 1.2, generally 1.0, similar to natural viral envelopes. The particles also have a homogenous size structure similar to that of natural viral particles and a physically stable unilamellar membrane structure. One or more proteins can optionally be incorporated into the AVE.

The following is a description of lipid vesicles in general and AVE in particular which can be prepared by a double detergent dialysis method. The first step of is the preparation of lipid vesicles without glycoprotein from a detergent-solubilized lipid mixture at a unique lipid: detergent ratio. Next, glycoproteins are inserted into the preformed vesicles by partial micellation with another detergent followed by dialysis. The process can reproducibly yield both small (<5 ml) laboratory scale samples as well as sterile large batches (>100 ml). The two steps are independent processes. Thus, a large reservoir of concentrated lipid envelopes can be prepared and stored while individual batch sizes of the final envelope containing the surface protein, or the desired composite epitopes of surface proteins, can be prepared upon demand. The artificial viral envelopes can be characterized by: (i) an advantageous phospholipid: cholesterol ratio of about 1:1; (ii) a virus-specific phospholipid composition; (iii) a homogenous size distribution around 250 nm, similar to natural viral size; (iv) a uniquely stable, rigid, unilamellar structure; (v) envelope glycoproteins such as the HIV-1 gp160, RSV G (aggregation) and F (fusion) proteins, and others, inserted in the outer surface; (vi) high fusogenic activity; (vii) specific binding to their monoclonal antibodies confirming the intact conformation of the surface glycoproteins; and (viii) selective binding to cell surface receptors such as the CD4 receptor on human T-cells. In some embodiments, the phospholipid composition of the synthetic viral envelopes are similar to the natural viral composition and comprise phosphatidylcholine (PC), phosphatidylserine (PS), phosphatidylethanolamine (PE), and sphingomyelin (SM). The envelope may further comprise additional lipids such as phosphatidylinositol. The double-dialysis method consists essentially of two steps: (1) preparation of the phospholipid/cholesterol envelope by solubilization of the lipids and cholesterol with sodium cholate or other appropriate detergent as the solubilizing agent at a unique molar ratio of approximately 45:1, followed by removal of the detergent by exhaustive dialysis against phosphate-buffered saline (PBS); and (ii) insertion of protein(s) in the outer surface of the preformed vesicles by partial micellation with sodium deoxycholate or other appropriate detergent at an approximate ratio of 8:1 and removal of the detergent by exhaustive dialysis as before in step (i). As would be appreciated by a person skilled in this art the term "partial micellation" refers to a vesicle membrane which is "softened" to the point that the vesicle flattens out and acquires a disc- or dumb-bell-like shape which reverses into a vesicular structure upon removal of the detergent; however, the vesicles are not solubilized (micellized) to the point that they lose their intrinsic bilayer structure and become true mixed micelles again. This process can be controlled by monitoring the scattering of light of the vesicles using a laser light scattering instrument. Enough detergent is introduced into the vesicle dispersion to maintain the light scattering signal. Loss of the light scatter signal indicates true solubilization, thus excess of detergent and loss of the vesicular structure in favor of a micellar structure. In the specific system exemplified herein, the preferred molar ratio of detergent:lipid that maintains the partially micellated disc-like vesicular structure was found to be about 8:1. The method of the subject invention can be readily modified by a person skilled in the art to use, for example, other solublizing agents or buffers. Generally, the proteins which are inserted into the preformed vesicles will be glycoproteins but other proteins can be used, so long as they remain inserted in the lipid vesicle. In the first step of the method, the detergent:lipid ratio can be from about 30:1 to about 60:1 and is preferably from about 40:1 to about 50:1 and is most preferably approximately 45:1. Use of detergent to lipid ratios in the 40:1 to 50:1 range is preferred. For the second dialysis step, the detergent: lipid ratio can be from about 5:1 to about 10:1 and is most preferably about 8:1. Useful detergents are well known to those skilled in the art and include, but are not limited to, bile salts (sodium cholate, deoxycholate, taurocholate, etc.), CHAPSO, octylglucoside, TRITON-X derivatives, etc. These detergents can be anionic such as CHAPSO, or nonionic such as octylglucoside or Triton-X. The selection of the detergent is determined taking into account the compatibility of a particular detergent with the surface protein to be inserted. Dialysis and related methodologies can be carried out using any of a number of techniques which are known to those skilled in the art. For example, bag, disc, flow-through, and counter-flow dialysis techniques and apparatus may be utilized. A wide range of lipid:protein molar ratios can be used. This range may be, for example, from about $1\times10^6$:1 or higher to around 100:1 or lower. The ultrastructure should preferably be unilamellar, however, oligolamellar may also be acceptable for some purposes. An important aspect of the double-detergent dialysis method is that the two steps are independent processes. During the first step, unilamellar lipid envelopes in a size range of about 50 to about 500 nm or, preferably, about 150 to about 350 nm or, most preferably, approximately 250 nm, essentially identical to natural viral membranes, are generated. These preformed envelopes are of superior physical stability with an average size, and size distribution, that remain essentially unchanged over several months when stored under refrigeration.

The envelopes produced according to the subject invention can be freeze-dried and thus preserved for extended periods of time. The freeze-drying, or other means of preservation, can be done either before or after insertion of the protein onto the envelope. The method is flexible so that batch sizes in a range of less than 5 ml to liter quantities can be prepared reproducibly and under sterile conditions using, for example, either teflon dialysis cells or flow-through hollow fiber dialysis apparatus.

A moiety which facilitates entry into a particular cell type or types can be included in the delivery vehicle. For example, a polynucleotide can be complexed with a carrier molecule (e.g., a lipid, an antibody or a receptor ligand or a combination thereof) which facilitates delivery to cells of a subject for the purpose of altering the biological properties of the cells. Polynucleotides can be modified to allow coupling of the nucleic acid compounds to a carrier molecule, for example a protein, lipid, or derivative thereof. Exemplary protein carrier molecules include antibodies specific to the cells of a targeted cell or receptor ligands and other molecules capable of interacting with receptors associated with a cell of a targeted epithelial cell, e.g., carbohydrates (mannose, asialoglycoproteins), hormones, transferring, viral surface glycoproteins. Alternatively, the polynucleotide may be naked (i.e., not encapsulated), or may be provided as a formulation with cationic compounds (e.g., dextran sulfate, DEAE-dextran, or poly-L-lysine). Another means of effecting cell type-specific expression of a delivered polynucleotide is incorporation of a cell type-specific transcriptional regulatory element (i.e., promoter and/or enhancer) into the polynucleotide, operably linked to the coding region of interest (i.e., the coding region whose expression is desired).

The polynucleotides can be coated with agents which enhance their uptake, and can be included within liposomes or artificial viral envelopes. Useful agents include cationic phospholipids, neutral phospholipids, lipids and mixtures thereof. Additional components may be included, such as targeting peptides or proteins, fusion peptides (e.g. from Sendai virus or influenza virus, envelope proteins of viruses, polycationic substances such as poly-L-lysine or DEAE-dextran, molecules which bind to the surface of airway epithelial cells including antibodies, adhesion molecules and growth factors, and the like).

Administration

The precise amount of polynucleotide administered (inhaled) will vary greatly according to a number of factors, including the type of polynucleotide being used, the susceptibility of the target cells to introduction of the polynucleotide, the size and weight of the subject, and the condition to be treated. The amount delivered is a function of the concentration of the formulation and the number of inhalations. The total dose is governed by the nature of the disease being treated. The minimum amount delivered is that which can produce a therapeutically useful effect. The maximum dose is governed by toxicity, and by economic considerations. It is possible to deliver up to hundreds of milligrams of a polynucleotide via inhalation.

When administering a polynucleotide using an inhalation device, the entire dosing event can involve the administration of anywhere from 10 µl to 1,000 µl, but more preferably involves the administration of approximately 50 µl to 10,000 µl of formulation. The entire dosing event may involve several inhalations by the patient, with each of the inhalations being provided using the same or different volumes of aerosol and aerosol free air.

One of ordinary skill in the art will be able to readily design effective dosing protocols. An effective dose delivered will usually be in the range of about 1 mg/dosing event to about 500 mg/dosing event, although more or less may be found to be effective depending on various factors, including, but not limited to, the subject's weight, and the desired result. If necessary, dosing can be repeated, based on the subject's response to initial or subsequent dosings. The success of a given dosing event can be measured by various parameters, including, but not limited to, detection of a polynucleotide and/or polypeptide encoded by the polynucleotide delivered, using well-known methods as described above; assessment of various physiological parameters, such as, for example, lung function (e.g., after delivery of polynucleotides encoding functional CFTR to a cystic fibrosis patient); detection of cancerous cells (e.g., after delivery to a subject of a polynucleotide specific for cancer therapy); or the presence of any new phenotype which occurs as a result of expression of the delivered polynucleotide.

Formulations

Delivery vehicles comprising polynucleotides can be administered alone, or in any pharmaceutically acceptable carrier, and in a variety of forms, including aqueous solutions, and dry powders. A buffer can be included in any of these formulations. Suitable buffers include phosphate, citrate, acetate, and Tris-HCl, typically at concentrations from about 5 mM to 50 mM, and in pH range from about 4 to about 10. Salts may also be included. Suitable salts include sodium chloride, sodium carbonate, calcium chloride, and the like.

For aqueous solutions, the polynucleotides may be dissolved in water or a buffer and formed into small particles to create an aerosol which is delivered to the subject. Alternatively, the polynucleotide may be in a solution or a suspension wherein a low-boiling point propellant is used as a carrier fluid. Suitable aerosol propellants include, but are not limited to, chlorofluorocarbons (CFC) and hydrofluorocarbons (HFC), a variety of which are known in the art.

The polynucleotide may be in the form of a dry powder which is intermixed with an airflow in order to provide for delivery of polynucleotide to the subject. Respirable dry powders within the desired size range can be produced by a variety of conventional techniques, including jet-milling, spray-drying, solvent precipitation, and the like. Powders are generally combined with a pharmaceutically acceptable dry bulking powder, with the polynucleotide present usuallat from about 1% to 10% by weight. Examples of dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Regardless of the formulation, it is preferable to create particles having a size in the desired range, which is related to airway diameter of the targeted region(s), as discussed above.

One or more surfactants, including, but not limited to, those described in U.S. Pat. No. 5,855,913, can be included in the formulation of the delivery vehicle. Aerosol dosage and formulations may be selected for a particular therapeutic application, as described, for example, in Gonda (1990) "Aerosols for deliver of therapeutic and diagnostic agents to the respiratory tract" in Critical Reviews in Therapeutic Drug Carrier Systems 6:273–313; and in Moren (1985) "Aerosol dosage forms and formulations" in Aerosols in Medicine: Principles, Diagnosis and Therapy", Moren et al., eds. Elsiever, Amsterdam.

If desired, other compounds of therapeutic value may be included in the formulations comprising polynucleotides. For example, a respiratory drug can be included. Useful "respiratory drugs" include those which are listed within the Physician's Desk Reference (most recent edition). Such drugs include beta adrenergic agonists which include bronchodilators; steroids, including corticosteroids; peptide non-adrenergic non-cholinergic neurotransmitters and anticholinergics; anti-inflammatory drugs; antiasthmatics; leukotriene (LT) inhibitors, vasoactive intestinal peptide (VIP), tachykinin antagonists, bradykinin antagonists, endothelin antagonists, heparin furosemide, anti-adhesion molecules, cytokine modulators, α-antitrypsin and disodium cromoglycate (DSCG).

The instant invention is shown and described herein in which is considered to be the most practical and preferred embodiments. It is recognized, however, that departures may be made therefrom which are within the scope of the invention and that obvious modifications will occur to one skilled in the art upon reading this disclosure.

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for Unless indicated otherwise, parts are parts by weight, molecular weight is weight average molecular weight, temperature is in degrees Celcius, and pressure is at or near atmospheric.

EXAMPLE 1

Formulation of the Polynucleotide

DNA was formulated with an artificial viral envelope (AVE) as the non-viral vector, using the double-dialysis method described above. The AVE formulation was modified by the addition of a cholesterol analog to the lipid membrane in order to increase the rigidity of the bilayer and provide a more stable formulation. Plasmid cDNA (total length approximately 7.5 kb) comprising β-galactosidase (β-gal) gene as a reporter under the control of CMV promoter was condensed with protamine sulfate and complexed with a negatively charged liposomal formulation (AVE) consisting of DOPE, DOPC, and cholesteryl glutarate, and a fusogen, in equimolar ratios, prepared by the double dialysis method. The resulting AVE/DNA formulation was packaged in blister packs containing a 45 μl unit dose reservoir, for use in the AERx™ (Schuster et al. (1997)) delivery system.

EXAMPLE 2

Stability of the AVE/DNA Within the Blister Pack

To determine the compatibility of the AVE/DNA with the AERx™ blister pack, the AVE/DNA formulation described in Example 1 was packaged and stored at 5° C. for 3 days. The size and surface charge (zeta potential) of the AVE was determined and compared to a freshly made sample which had also been packaged in the AERx™ blister material. The results are shown in Table 1.

TABLE 1

| Mean Diameter (nm) | | Zeta Potential (mV) | |
|---|---|---|---|
| Day 0 | Day 3 | Day 0 | Day 3 |
| 435 | 326 | +23.71 | +20.02 |

To further assess the nonreactive nature of the blister material, AVE which had been packaged within the blister for several hours or for 3 days was removed from the blister and used to perform an in vitro transfection of 293 cells. The results are shown in Table 2.

TABLE 2

| % Transfection Activity in 293 Cells Compared to a Freshly Prepared AVE | |
|---|---|
| Day 0 | Day 3 |
| 91.7 ± 6.9 | 99.0 ± 17.1 |

EXAMPLE 3

Extrusion of the Formulation Through a Nozzle

Two AERx™ nozzle arrays, having either small (14 μm) or large (2.2 μm) holes, were tested for their effect on the integrity of naked DNA or AVE/DNA following forcible extrusion. The DNAs were also tested for their ability to clog the nozzles. Extruded samples were collected in sterilized collection tubes. The holes in the nozzle array were not blocked with either formulation. The integrity of the DNA was monitored using gel electrophoresis and ethidium bromide staining. The naked DNA remained intact after extrusion through the nozzles. The integrity of the AVE/DNA formulation could not be assessed using electrophoresis, as the formulation did not migrate in the gel, or allow ethidium staining of the condensed DNA. The integrity of the AVE/DNA formulation was measured as described in the next example.

EXAMPLE 4

Extrusion and Aerosolization onto 293 Cells 293 cells were grown on glass coverslips and placed on stage 5 of an Anderson cascade impactor to assess the effect on cell viability following extrusion and aerosolization of 10 mM Tris onto the cells. Aerosolization was performed at 70 L/minute and 50 L/minute to determine the cells' tolerance to these flow rates. The results are shown in Table 3.

TABLE 3

| | % Viability |
|---|---|
| Untreated Cells | 84.3 ± 6.4 |
| Tris 10 mM. 50 L/min | 82.6 ± 2.6 |
| Tris 10 mM. 70 L/min | 69.9 ± 15.7 |

EXAMPLE 5

Transfection of 293 Cells with Extruded DNA

Extruded DNA samples containing β-gal expression constructs were collected and allowed to contact 293 cells in in vitro culture. After transfection, β-galactosidase activity was determined using standard methods, as was total cellular protein. The results are shown in FIG. 1. Naked DNA was not found to cause measurable expression of β-gal in 293 cells ("No AVE" in FIG. 1). AVE/DNA did cause significant expression of β-gal in 293 cells, and the level of expression was not significantly decreased by extrusion through either the 1.4 or 2.2 μm nozzles, as shown in FIG. 1. Cell viability was not significantly affected by the treatment, although a slight decrease in viability was seen in experiments where the aerosol was allowed to directly impact coverslip-grown cells in a high flow-rate airstream. A slight reduction in flow of the airstream allowed full viability.

While the present invention has been described in some detail with reference to specific embodiments thereof, it should be understood by those skilled in the art that various changes may be made and equivalents may be substituted without departing from the true spirit and scope of the invention. In addition, many modifications may be made to adapt a particular situation, material, compositions of matter, process, process step or steps, to the objective, spirit and scope of the present invention. All such modifications are intended to be within the scope of the claims appended hereto.

What is claimed is:

1. A method of targeting an area of a patient's respiratory tract, comprising:
   aerosolizing a formulation to create aerosol particles comprised of polynucleotides and a polynucleotide condensing agent complexed with negatively charged phospholipids comprising cholesteryl glutarate, wherein the condensing agent is protamine sulfate which condenses the polynucleotides to a size in a range of from about 20 to about 50 nanometers;
   adjusting an aerodynamic diameter of the aerosolized particles based on a targeted area of a patient's respiratory tract;
   inhaling a volume of aerosol particles of the formulation and aerosol-free air; and
   controlling the patient's inhaled volume of aerosolized formulation and aerosol-free air.

2. The method of claim 1, wherein the aerosol particle size is adjusted such that the aerodynamic diameter of the aerosol particles is in a range of from 1–3 µm and alveoli of the patient's respiratory tract are targeted.

3. The method of claim 1, wherein the aerosol particle size is adjusted such that the aerodynamic diameter of the aerosol particles is in a range of from 4–6 µm and central airways of the patient's respiratory tract are targeted.

4. The method of claim 1, wherein the aerosol particle size is adjusted such that the aerodynamic diameter of the aerosol particles is in a range of from 7–10 µm and upper airways of the patient's respiratory tract are targeted.

5. The method of claim 1, further comprising:
adjusting the patient's inspiratory flow rate inside a range of about 0.10 to about 4.0 liters/second.

6. The method of claim 5, wherein the flow rate is adjusted inside a range of about 0.2 to about 3.0 liters per second.

* * * * *